United States Patent [19]

McStravick et al.

[11] Patent Number: 4,673,652

[45] Date of Patent: Jun. 16, 1987

[54] METHOD OF TESTING AND RECONDITIONING INSULATING TUBULAR CONDUITS

[75] Inventors: David M. McStravick, Houston, Tex.; David V. Chenoweth, Lahaina, Hi.; David M. Anderson, Whittier, Calif.

[73] Assignee: Baker Oil Tools, Inc., Orange, Calif.

[21] Appl. No.: 936,222

[22] Filed: Dec. 1, 1986

Related U.S. Application Data

[63] Continuation of Ser. No. 433,581, Oct. 12, 1982, abandoned.

[51] Int. Cl.[4] .......................................... G01N 33/18
[52] U.S. Cl. .................................... 436/2; 73/40.5 R; 73/40.7; 166/250; 138/149; 436/3; 436/39; 436/151; 436/167
[58] Field of Search ................. 73/40.5 R, 40.7 R, 23, 73/73; 166/202, 203, 250; 250/358.1, 359.1; 138/111, 149; 436/2, 3, 28, 39, 41, 42, 151, 164, 167, 169; 422/86

[56] References Cited

U.S. PATENT DOCUMENTS

| | | | |
|---|---|---|---|
| 2,940,302 | 6/1960 | Scherbatskoy | 250/358.1 |
| 3,194,310 | 7/1965 | Loomis | 166/250 |
| 3,364,993 | 1/1968 | Skipper | 73/40.5 R |
| 3,478,577 | 11/1969 | Hauk | 166/250 |
| 3,511,282 | 5/1970 | Willhite et al. | 166/303 |
| 3,585,963 | 6/1971 | Hiszpanski | 422/58 |
| 3,763,935 | 10/1973 | Perkins | 166/DIG. 1 |
| 3,771,349 | 11/1973 | Yatabe | 73/29 |
| 3,775,612 | 11/1973 | Foster et al. | 250/358.1 |
| 3,776,038 | 12/1973 | Elliott | 73/29 |
| 3,952,746 | 4/1976 | Summers | 604/361 |
| 4,041,437 | 8/1977 | Matsuara et al. | 73/29 |
| 4,060,263 | 11/1977 | Kotcharian | 138/149 |
| 4,285,369 | 8/1981 | Misiwa et al. | 138/111 |
| 4,287,753 | 9/1981 | Grantham | 73/29 |
| 4,288,653 | 9/1981 | Blom et al. | 73/40.5 R |
| 4,288,654 | 9/1981 | Blom et al. | 73/40.5 R |
| 4,326,404 | 4/1982 | Mehta | 73/29 |
| 4,332,170 | 6/1982 | Belval et al. | 73/40.5 R |
| 4,344,320 | 8/1982 | Haupt et al. | 73/40.7 |
| 4,362,939 | 12/1982 | Horiuchi et al. | 250/359.1 |
| 4,380,168 | 4/1983 | Ibe | 73/40.5 R |
| 4,381,452 | 4/1983 | Jeunehomme | 73/29 |
| 4,382,383 | 5/1983 | Buda et al. | 250/358.1 |
| 4,450,711 | 5/1984 | Claude | 73/40.5 R |

FOREIGN PATENT DOCUMENTS 2236944 2/1974 Fed. Rep. of Germany ...... 166/250

OTHER PUBLICATIONS

Oil & Gas Journal, 7/26/77, pp. 113–121.

Primary Examiner—Michael S. Marcus
Attorney, Agent, or Firm—Norvell & Associates

[57] ABSTRACT

A non-destructive on-site method of inspection, and testing of the insulating performance and reconditioning of a concentric insulating tubular conduit member is disclosed. The insulating tubular conduit members comprise concentric walled members with an intermediate annular insulating cavity defined therebetween. This non-destructive method of testing and inspection is based on a determination of the presence of an unacceptable level of moisture in the annular insulating cavity. Visual, auditory, electrical, and radioactive indicating means can be employed in accordance with the principles of this invention. The use of a vacuum pump to establish at least a partial vacuum in the annular insulating cavity in conjunction with the testing technique employed herein, additionally provides a means for reconditioning and improving the insulating performance of insulating tubular conduits and permits reassembly of a fluid transmission conduit in which each of the tubular conduit sections will have the desirable insulating capacity.

1 Claim, 10 Drawing Figures

METHOD OF TESTING AND RECONDITIONING INSULATING TUBULAR CONDUITS

This is a continuation of application Ser. No. 433,581 filed Oct. 12, 1982 abandoned.

BACKGROUND OF THE INVENTION

1. FIELD OF THE INVENTION

This invention relates to insulating tubular conduits for use, especially in subterranean oil wells, and to an indirect method of inspecting and testing insulating tubular conduits to determine if their insulating performance is satisfactory.

2. DESCRIPTION OF THE PRIOR ART

One technique for recovering viscous oil deposits is to heat the crude deposits thus reducing their viscosity and permitting them to flow to the surface. One method of heating the subterranean deposits is to inject superheated steam through an injection well communicating with the viscous crude. The heated oil can then flow to the surface in the injection well or in other wells communicating with the producing formation. Although not new, such steam injection techniques have not heretofore been commercially competitive because of the relatively high cost of steam injection equipment and because of the large heat loss which may occur between the point at which the super heated steam is injected and the formation.

One means of reducing the transmission heat losses is the use of concentric wall insulated tubing. Examples of concentric wall insulated tubing are shown in U.S. Pat. No. 3,511,282 and the insulated tubing design sold by the General Electric Company under the trademark Thermocase. A concentric wall thermal insulated conduit is also disclosed and claimed in U.S. patent application Ser. No. 272,411 filed on June 10, 1981. Each of these designs employs a plurality of individual tubular sections which, when attached end to end in tandem relationship, form a fluid transmission conduit or tubing string. Each of these designs also employs inner and outer tubular members attached adjacent their ends to define an annular insulating cavity extending along substantially the entire length of each section. Conductive, convective and radient insulating barriers or material may be located within each insulated cavity. Inert gases resistant to the transmission of heat through the cavity may also be employed in the cavity. Since the cavities are hermetically sealed at least a partial vacuum may be established within the annular insulating cavity to prevent heat loss.

As with many tools used in subterranean wells, concentric wall insulated tubing can be expected to undergo degradation during its useful life and the insulating properties of all types of tubing sections can be expected to deteriorate. Continuous steam injection can be expected to result in a reduction of the insulating performance of any insulating tubing design before the tubing members themselves become unusable. The tubing members represent a significant part of the cost of an insulating tubing joint. One significant problem would involve the deterioration of the welds or other means of sealing the annular insulating cavities at the points where the inner and outer tubing are attached to each other. Given the fact that the tubing is used for steam injection, it could be expected that a large amount of moisture would develop in the annular insulating cavity if the welds deteriorated.

Since it would be desirable to reuse the rather expensive insulating tubing sections and because the tubing members themselves would not be expected to deteriorate before the insulating performance reached an unacceptable level, some method of non-destructive testing to determine insulating performance is necessary. Ideally a method of on-site testing which can be utilized each time the tubing sections or joints are removed from the well would be useful. One method of indirectly determining the insulating performance of an insulating tubular member is to utilize temperature recorders affixed to the exterior of the outer tubular member in each section. These temperature recorders, of the type shown in U.S. Pat. No. 3,002,385, are of such a composition as to change, color when the temperature reaches a certain level. Thus removal of the tubing and monitoring of these temperature recorders will indicate the maximum temperature of the outer tubing member. When the temperature has reached an undesirable level it would be assumed that the insulating performance of that particular joint is defective. However, this method assumes that the heat transfer causing the outer tubular section to reach an elevated temperature is due to heat transfer through the annular insulating cavity. There are, however, other components in a fluid transmission conduit or well completion which could cause the outer tubing member to reach undesirable elevated temperatures. For example, a leak in the coupling member between joints could expose the tubing members to steam which has leaked through the coupling to the annulus. A defective or leaking packer would also permit steam to rise from the producing formation into the annulus above the packer and would also result in a faulty indication that the tubing joints were defective. The non-destructive testing and inspection method disclosed herein allows indirect evaluation of the heat transfer through the annular insulating cavity of each tubing section, without the introduction of error due to leaks in the tubing coupling, the packer, or other components of the fluid transmission conduit.

SUMMARY OF THE INVENTION

The preferred embodiments of this invention provide a non-destructive method of indirect on-site inspection and testing of the insulating cavity of a tubular fluid transmission conduit. Individual inspection of each insulating tubing section or tubing joint can be conducted at the surface site of the well when tubing joints are removed from the well. The annular insulating cavity in each concentric wall tubular member may be exposed to a precalibrated moisture sensitive device to determine the amount of water, in the liquid and vaporous state, present in the annular cavity. Since moisture would constitute the predominate heat transfer mechanism within the annular insulating cavities, the presence of more than a predetermined amount of water in the annular insulating cavity of any tubular section or joint would establish that that section was defective. The pre-calibrated moisture sensitive device could be responsive to changes in either visual, auditory, radiation, electrical, or other property which would depend upon exposure of the device to moisture.

In one embodiment of this invention, the moisture sensitive means would be enclosed within the annular insulating cavity and its change in state would be monitored after the tubing was removed. In another embodiment, exposure of the annular insulating cavity to the moisture sensitive device would occur only after removal of the tubing from the well. In one embodiment, exposure would occur when communication was established between the annular insulating cavity and a vacuum pump. The vacuum pump would remove any undesirable moisture from the annular insulating cavity, and if the moisture sensitive device indicated that more than a pre-determined amount of moisture had been present, remedial steps could be taken to improve the integrity of the joint. The principle remedial step which could be taken would be to improve the seal between the inner and outer tubing members defining the annular insulating cavity since this seal or weld would constitute the principle leak path. This method would provide not only a means of improving the integrity of the defective sections, but it would also improve the insulating performance of the tubing by removing undesirable moisture from the annular insulating cavity.

BRIEF DESCRIPTION OF THE DRAWINGS

FIG. 6 and 6a illustrate the use of an electrical member for determining the presence of an unacceptable of moisture in the annular insulating cavity.

DESCRIPTION OF THE PREFERRED EMBODIMENTS

Figure 1:
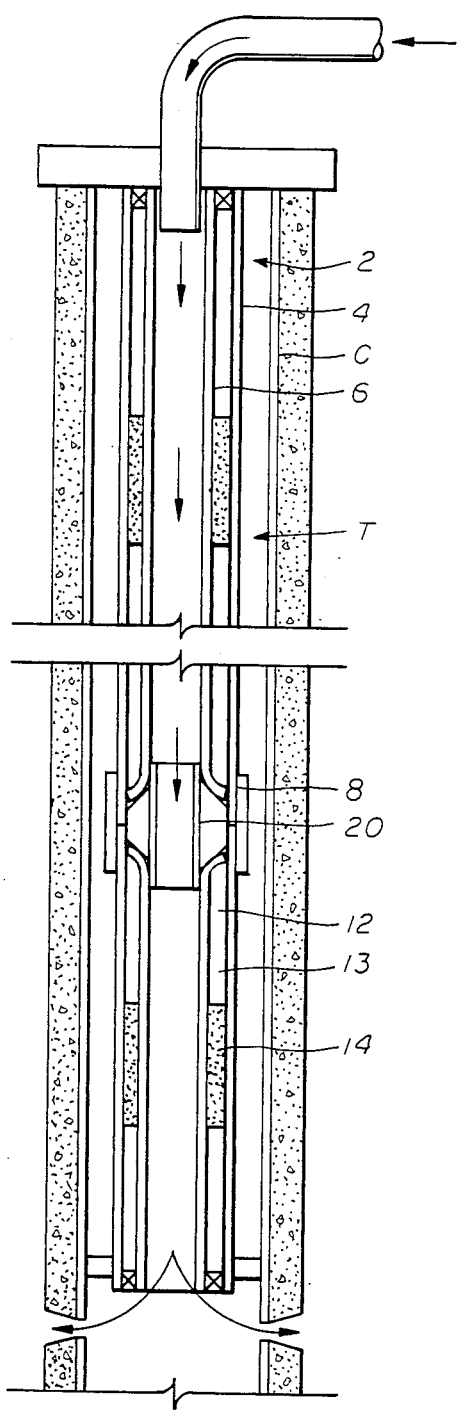
FIG. 1 is a schematic illustrating the injection of steam through a fluid transmission conduit or tubing string formed of individual tubing sections or joints.

FIG. 1 illustrates, in schematic form, the use of a plurality of sections comprising concentric walled insulating tubing members comprising an insulating tubing string or fluid transmission conduit. The tubing string T, shown in FIG. 1, permits the injection of steam at the surface of the well through the tubing to the formation therebelow. The insulating tubing string ensures that the heat loss between the surface and the formation will not be so excessive as to defeat the function of steam injection. The tubing string T, comprising a plurality of individual insulating tubing sections or joints 2, is positioned within the well and within the well casing C in much the same manner as a conventional tubing string.

Figure 2:
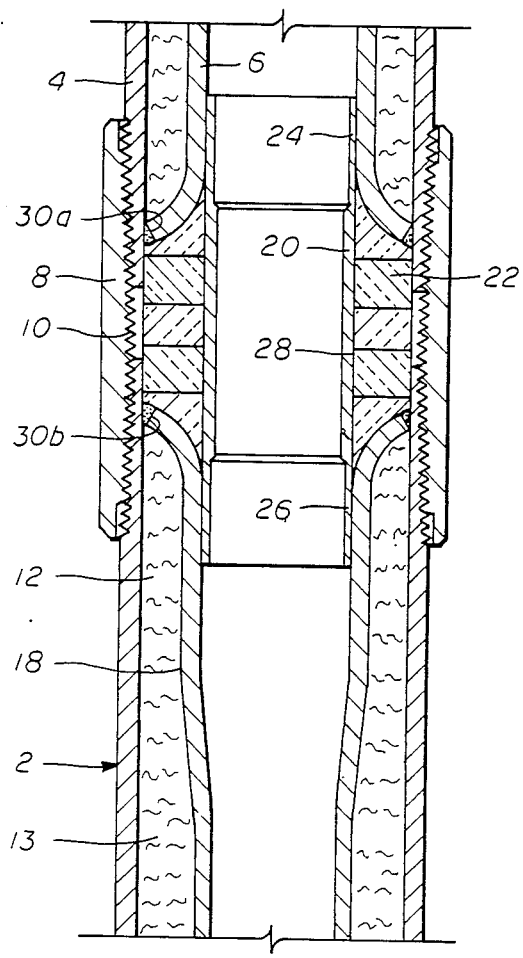
FIG. 2 shows two tubing sections coupled at their ends and illustrates the annular insulating cavity in a typical tubing section.
Figure 2:
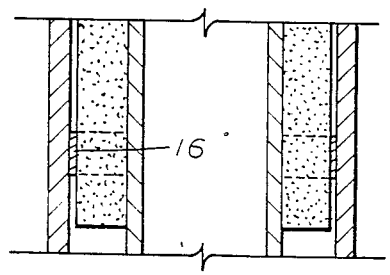

FIG. 2 shows the components of individual sections or joints and the interconnection between adjacent abutting tubular sections. It will be understood that the opposite ends of each individual section is of generally the same configuration as is shown in FIG. 2. Each individual concentric insulating section 2 comprises an outer tubing member 4 and an inner tubing member 6. The outer tubing 4 comprises a straight cylindrical member having conventional threads 10 at each end. A conventional external coupling 8, engaging threads 10, can be used to join adjacent concentric members. In order to reduce the number of welds needed to secure inner tubing 6 to outer tubing 4, the end of inner tubing 6 is outwardly flared, as shown in FIG. 2. A single circular face weld 30 can then be made between inner tubular 6 and outer tubular member 4.

In the assembled configuration of a single insulating tubing section or joint, as shown in FIG. 2, an annular cavity 13 is formed between outer tubing 4 and inner tubing 6. This annular cavity 13 may be filled with thermal insulation. In the form of insulating tubing shown herein, this thermal insulation comprises a combination of a blanket insulation 12 having ceramic fibers, at least one rigid insulating member 14, and a reflective heat shield 18. At least one rigid cylindrical insulating member 14 is located within annular cavity 13 between the welded ends joining outer tubing 4 to inner tubing 6. A molded, high temperature pipe and block insulating composed by hydrous calcium silicate such as molded calcium silicate member 14 would provide structural support between inner tubing member 6 and outer tubing member 4 between the ends of annular cavity 13. Calcium silicate could be used as the primary insulating material. In the configuration depicted herein, insulating member 14 comprises a conventional pipe and block insulating member which is commercially available. One molded calcium silicate pipe and block insulating member that can be used is manufactured by Johns-Manville and is commonly referred to under the trademark "Thermo-12". These standard pipe and block insulation members are available in half-sections which can be positioned in surrounding relationship with respect to inner tubing 6. Metal bands 16 can then be attached around the periphery of the two half-sections to form a single annular insulating member structurally supporting the outer tubing 4 relative to the inner tubing 6.

The remainder of annular cavity 13 contains a blanket insulation 12, which is also commercially available. Thermal insulating blankets, composed of long mechanically bonded refractory fibers providing a combination of high blanket strength, flexibility and high thermal performance, are commercially available. In the form of this insulating tubing shown herein, a thermal insulating blanket of the type manufactured by Johns-Manville under the trademarks "Thermo-Mat" or "Ceratex", has been employed to form a convective insulating barrier within annular cavity 13. This insulating blanket 12 can be secured to inner tubing 4 by wrapping a conventional glass fiber tape around the exterior of the insulating blanket 14. When employed in combination, blanket insulation 12 and the rigid calcium silicate insulating member 14 should substantially fill annular cavity 13 between the inner and outer tubings. Insulating performance can be further enhanced by filling the annulus with an inert gas or establishing at least a partial vacuum therein.

In addition to the convective insulating barriers provided by blanket insulation 12 and rigid insulating member 14, a radiant reflective heat shield member 18 can be provided. In the form of this insulating tubing shown herein, this reflective heat shield is incorporated on the outer surface of inner tubing 6, and comprises a material having a relatively low thermal emissivity. In this form, aluminum foil has been applied around inner tubing 6. This aluminum foil comprises a reflective surface which will further reduce the heat transfer of this tubing assembly.

Annular cavity 13 provides sufficient space to contain insulation for maintaining appropriate heat transfer characteristics over most of the length of this tubing. There does, however, remain a space between interior flared ends on adjacent tubing members. An interior coupling or cylindrical spacer member 20 can be employed to completely isolate the area otherwise bounded by the flared inner tubing ends of adjacent conduits and the outer coupling 8. This interior coupling 20 comprises a cylindrical member having outer sections 24 and 26 having a thickness which is less than the thickness of the central section 28 of the interior coupling member. As shown in FIG. 2, the ends 24 and 26 can be wedged into engagement with the tapered section 34 of each inner tubing member 6. Insulation can then be positioned around the exterior of interior coupling 20 to reduce heat loss in the vicinity of the coupling. In the form of this insulating tubing shown herein, blanket insulation of the same type as blanket insulation 12 used within annular cavity 13 can be affixed around interior coupling central section 28 in a donut fashion. The blanket insulation then fills the cavity bounded by the radiused ends of adjacent interior tubing members and the interior and exterior coupling members. An assembled tubing string or conduit comprising a plurality of individual insulating tubing conduits 2 would then have insulating material positioned within the annular space between inner tubing 6 and outer tubing 4 along substantially the entire length of the insulating tubing conduit 2. Finally, a second low emissivity barrier or radiant heat shield is provided on the exterior of the outer tubing. The outer tubing can be painted along its entire length to provide this barrier. Two low emissivity barriers will then act to reduce heat transfer over most of the tubing.

This combination of convective, conductive and radiant insulating barriers contained in the annular insulating cavity 12 of the form of insulating tubing shown herein, is highly effective in providing insulation between inner tubing member 6 and outer tubing member 4 for a reasonable time after insertion of the tubing sections and fluid transmission conduit into the well. However, the use of these materials in tubing for the injection of fluids, especially steam, results in a moisture laden environment. During the use of any form of insulating tubing currently available, it is possible that leaks would develop and moisture would be introduced into the annular insulating cavity 12. The primary leak path through which moisture would be introduced would be local defects or pinholes in the seals between the tubular members, here the welds 30a and 30b located at the opposite ends of the annular insulating cavity 12. Note, that the tendency of these welds or seals to deteriorate over the life of the tubing would be present not only with this form of insulating tubing, but with any concentric wall insulating tubing, regardless of the manner in which the inner tubing were attached to or sealed with the outer tubing. The presence of moisture in the annular insulating cavity 12 would account for the primary heat transfer mechanism existing in a defective tubing section 2. Moisture near the inner tubing member 6, which is exposed to superheated steam, would be vaporized. Water vapor which would then migrate to the outer tubing member 4, which normally would be at a temperature less than the boiling point of water would then condense on or adjacent outer tubing member 4, thus heating the outer tubing member. Thus when the moisture level in the annular insulating cavity 12 reaches an unacceptable level, individual tubing sections no longer adequately perform their insulating function.

Figure 3:
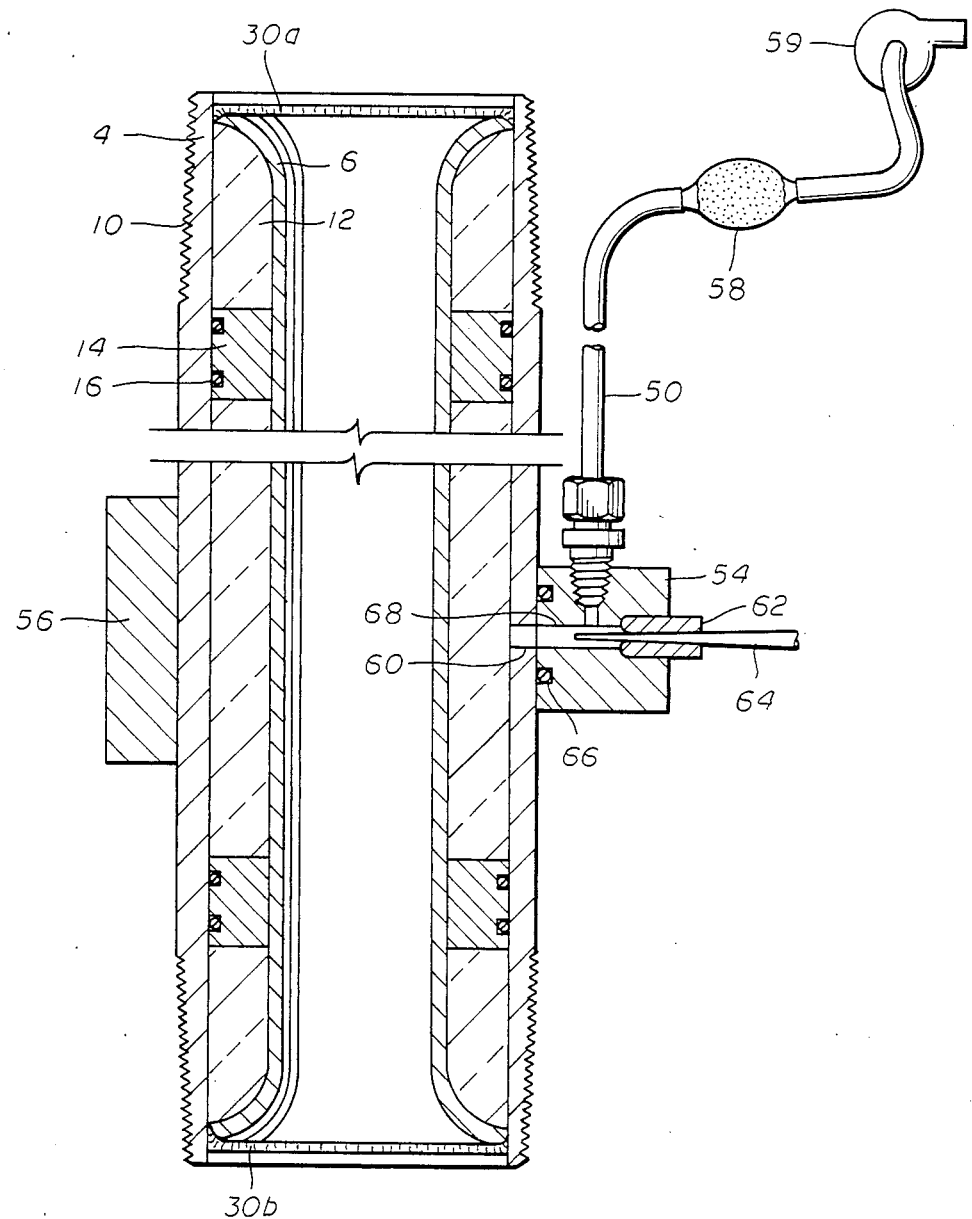
FIG. 3 illustrates the use of a vacuum pump to withdraw moisture from the annular insulating cavity and to determine the amount of moisture initially present in the insulating cavity.

Some means of non-destructive on-site testing is highly desirable to permit a rapid determination of which tubing sections are performing satisfactorily immediately after removal from the well. Since moisture constitutes the primary mode of heat transfer present in defective joints, a pre-calibrated moisture sensitive sensor or device exposed to the atmosphere in annular insulating cavity 12 would provide a means for indirect non-destructive testing and inspection of insulating tubing members upon removal from the well. Such moisture sensitive sensors can be visual, auditor, electrical, radioactive, or some other means for detecting and recording the levels of moisture present in the annular insulating cavity. In the preferred embodiments of this invention, these moisture sensitive sensors comprise one of several types. First, the moisture sensitive sensor may be of the type which can be introduced into the insulating cavity during fabrication of the device. For example, the auditory device shown in FIGS. 5 and 5a, the electrical device shown in FIG. 6, and the visual means shown in FIG. 7 can be introduced into the annular insulating cavity at the time the insulating joint is fabricated. Reaction of moisture with the moisture sensitive devices shown in FIGS. 5, 6 and 7 will result in a change which can be detected upon removal of the device from the well. The second type of pre-calibrated moisture sensitive sensor which can be used according to the principle of this invention would be a sensor which is exposed to the annular insulating cavity after removal of the tubular section from the well. FIGS. 3 and 8 illustrate a visual and a radioactive moisture sensitive sensor means which can be employed according to the principles of this invention. This neutron logging technique can also be used to detect the presence of excess moisture in the insulating cavities of the tubing string while in the well.

Figures 5, 5A:
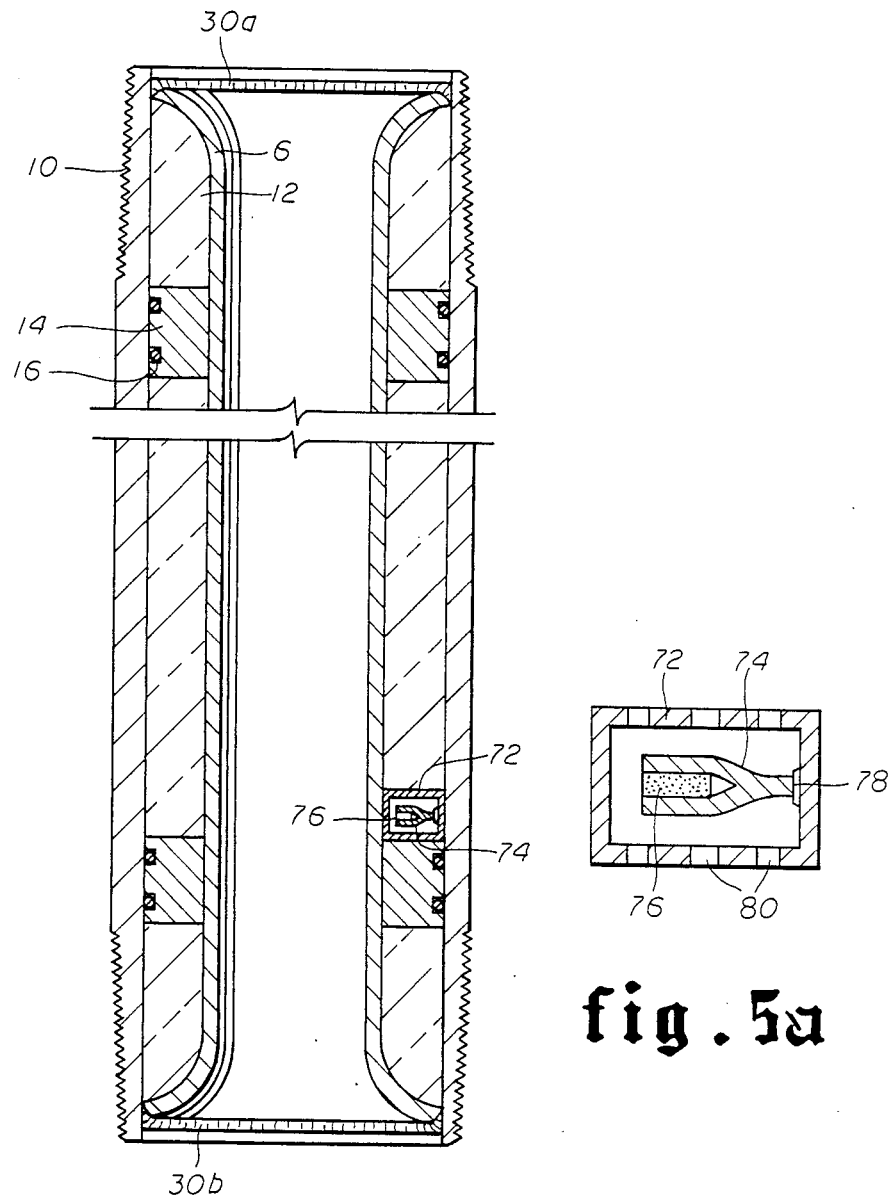
FIG. 5 and FIG. 5a illustrate the use of an auditory member to determine the presence of an unacceptable level of moisture in the annular insulating cavity.

The auditory sensitive member shown in FIG. 5 comprises a tuning fork 74 inserted in annular insulating cavity 12. The natural vibratory frequency of tuning fork 74 differs from the vibratory frequency of any of the other components in insulating section 2. As shown schematically in FIG. 5 tuning fork 74 is welded to a metallic member 72 enclosed in the annular insulating cavity. Member 72 is vented to the insulating cavity by means of ports 80 which insure that moisture existing in the cavity can communicate with the tuning fork. A moisture sensitive material 76 is initially bonded to the vibrating tines of tuning fork 74. This moisture sensitive keep 76 prevents vibration of tuning fork 74 until exposure to an unacceptable level of moisture causes a loss of cohesion 76 and adhesion between keep 76 and the tines of tuning fork 74. Thus the tines are free to vibrate, and upon removal of tubing section 2 from the well, a blow on the exterior of the tubing section will cause tuning fork 74 to vibrate at a unique frequency. This frequency can be detected, thus indicating that the particular tubing section no longer has the desirable insulating characteristics.

Figure 6:
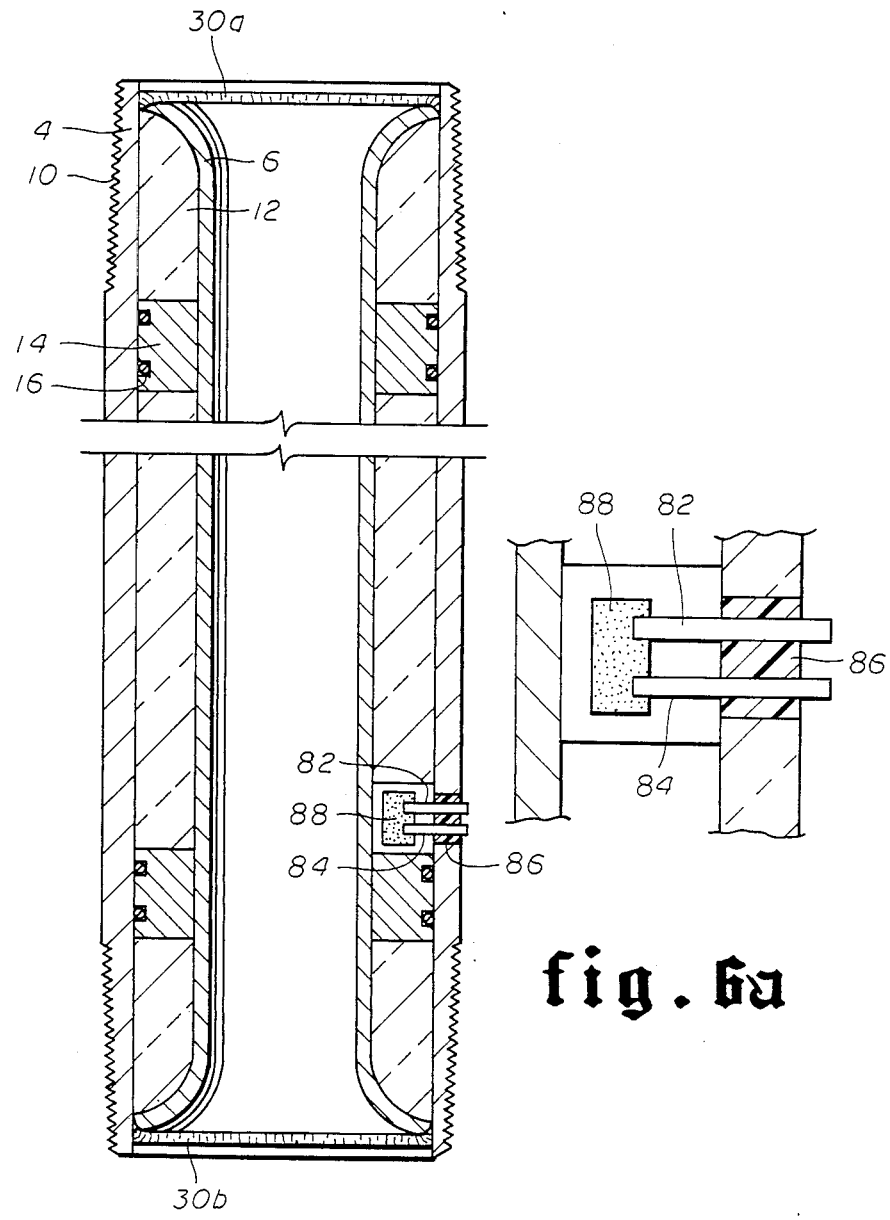

FIGS. 6 and 6a illustrate a device which relies on a change of electrical properties rather than auditory properties to detect an unacceptable level of moisture in the annular insulating cavity. In this device two electrodes 82 and 84 extend through an insulating member 86 in the outer insulating tubing 4. Adjacent the inner ends of electrodes 82 and 84 a member comprising a moisture sensitive material of known resistance is attached to both electrodes 82 and 84. This member 88, of known resistance, forms an electrical circuit between electrodes 82 and 84. Thus an attachment of an electrical source and a volt meter or other meter capable of detecting changes in electrical properties can be attached to the exterior of electrodes 82 and 84 to determine if member 88 is in place and if the circuit still has the same resistance as initially calibrated. If, however, member 88 is exposed to an unacceptable level of moisture the resistance of this material will change sufficient to alter the detectable electrical properties of the device. Note that any material for which any of the electrical properties change when exposed to an unacceptable level of material may be used and this change in electrical properties can be detected.

Figure 7:
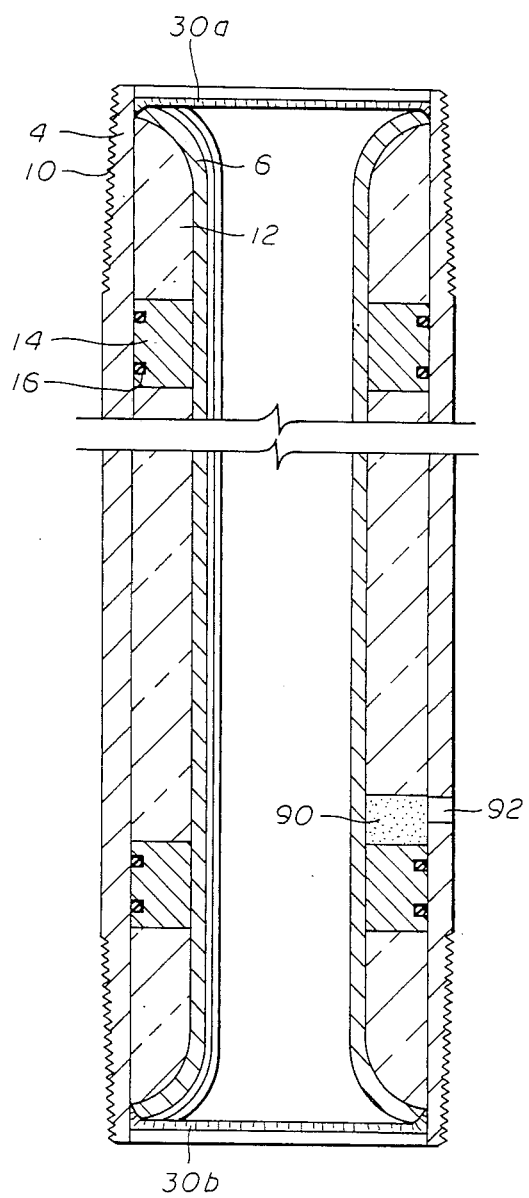
FIG. 7 illustrates the use of a visual member for indicating the presence of an undesirable level of moisture in the annular insulating cavity.
Figure 8:
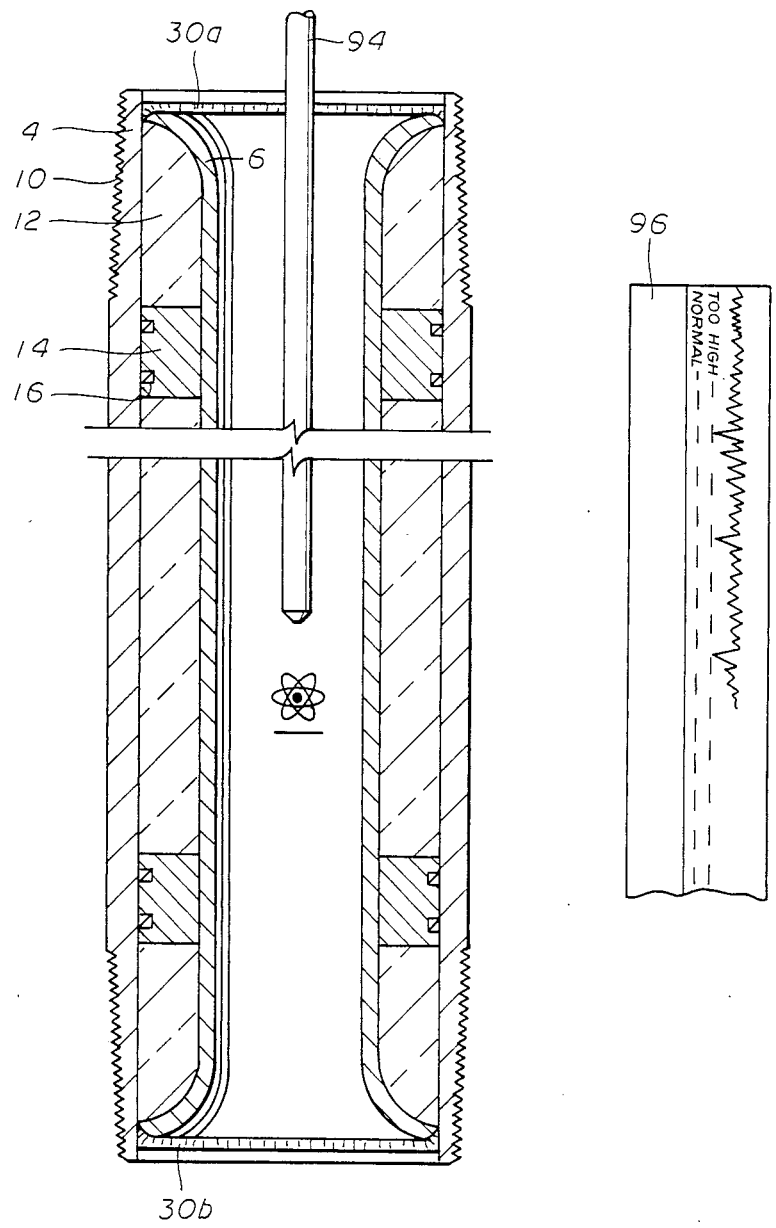
FIG. 8 illustrates the use of a radioactive source such as a source of neutrons for determining the presence of an unacceptable level of moisture in the annular insulating cavity.

In FIG. 7 a material which visually changes upon exposure to an unacceptable level of moisture is inserted in the insulating cavity 12 and a quartz window 92 is situated in the exterior of tubing 4. For example, material 90 may comprise calcium chloride with a moisture sensitive dye interspersed therein. This moisture sensitive dye would change color as the calcium chloride absorbs an unacceptable amount of moisture in the insulating cavity 12.

Figure 4:
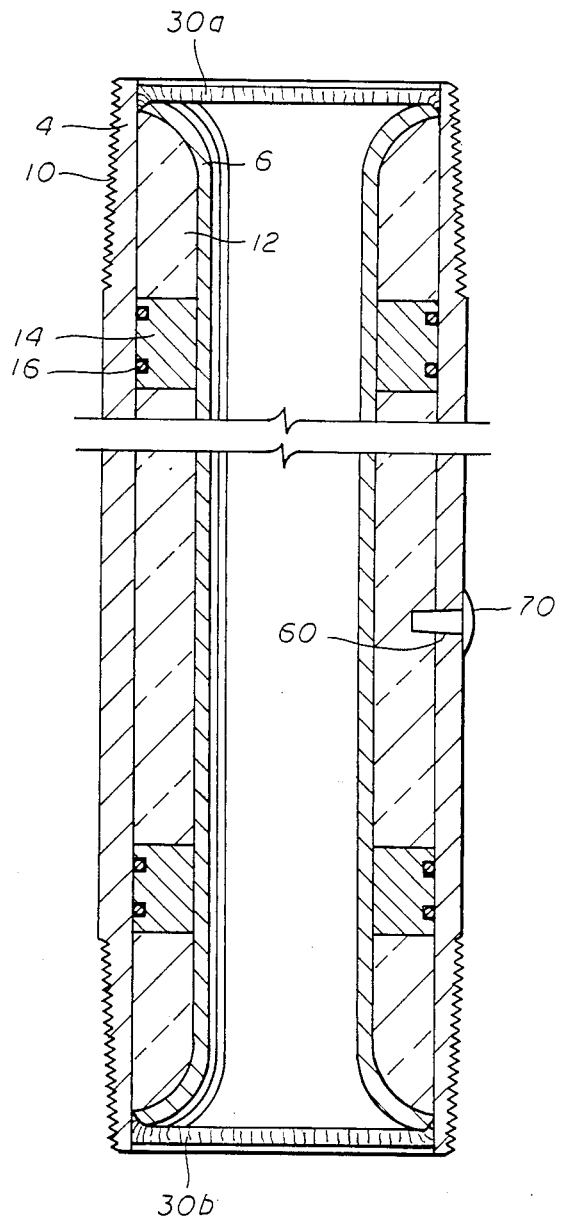
FIG. 4 shows the resealed insulating cavity after removal of moisture from the insulating cavity and the establishment of a partial vacuum together with the additional weld at the end of the annular insulating cavity.

Although the embodiments shown in FIGS. 5, 6 and 7 represent acceptable methods of determining the presence of an unacceptable level of moisture in the annular insulating cavity they are not reusable and it may be difficult to insert a new device if an unacceptable joint is refurbished and is used again. FIG. 3 illustrates one form of this embodiment which is reusable and combines both a means of detecting an unacceptable level of moisture in the annular insulating cavity and a means of restoring the insulating performance of the annular insulating material in cavity 12. The device depicted in FIG. 3 comprises a fixture 54 which can be attached to the exterior of a tubing section 2. This fixture 54 is in turn attached to a vacuum pump by means of a flexible hose 50. Intermediate the ends of flexible hose 50 is a receptacle 56 containing a moisture sensitive material such as the calcium chloride with a moisture sensitive dye similar to that described with a reference to the embodiment shown in FIG. 7. By drilling a hole in the outer tubing 4, communication can thus be established between annular insulating cavity 12 and the moisture sensitive material contained in vessel 56. Fixture 54, which receives tapered pin 64, can then be attached to the exterior of the tubing section in alignment with the drilled hole. As the vacuum pump removes both the air and moisture in annular insulating cavity 12, an unacceptable level of moisture passing through vessel 56 will cause a change in color of the material contained in vessel 56. It should be noted that an auditory, an electrical, a radioactive or some other moisture sensitive device in addition to this visual could be employed with this embodiment of the invention. When an acceptable vacuum has been established within insulating cavity 12 the puncture 60 can be sealed by driving pin 64 into hole 60. Pin 64 can then be severed flush with the exterior of outer tubing member 4 and welded as a back up means to maintain the vacuum in cavity 12. Evacuation of cavity 12 in this form of insulating tubing will improve the insulating performance to some degree but where an unacceptable level of moisture has been detected it becomes desirable to seal any leak paths which may exist and which have allowed moisture to enter cavity 12. The primary leak paths in this or any other of the invention will normally be the points of attachment between the inner tubing 6 and the outer tubing 4. It will thus be desirable to reseal or reweld these points of attachment to seal off any leaks which have developed over the life of the insulating tubing. Note that FIG. 4 shows an additional weld at 30a and 30b.

FIG. 8 illustrates another embodiment of this invention which can be used either alone or in conjunction with the vacuum process discussed with reference to FIG. 3. The embodiment of FIG. 8 comprises use of a radioactive source 94 and a means of recording the radioactivity passing through annular insulating cavity 12. If a neutron source is used and its effects subsequently recorded, as shown on the tape identified at 96 in FIG. 8, the presence of an undesirable amount of moisture in cavity 12 will affect the radioactivity detectable after passage through cavity 12. Conventional neutron well logging equipment operates in much the same manner for determination of the fluids in a downhole formation in a well. Neutron well logging is the study of formation-fluid-content properties in a subterranean well by neutron bombardment and the detection of resultant gamma radiation. This technique is also known as neutron logging. Adaptation of this technique to the problem now under consideration will provide one form of moisture sensitive indicator which can be employed pursuant to this invention. If excessive moisture is detected, by neutron bombardment or any other means, the performance of the joint may be improved by estalishing a vacuum within the annular insulating cavity. Rewelding the interconnections would also be desirable. This method of improving the performance of a used insulating tubing joint can be employed with tubing joints initially designed to operate with a partial vacuum in the annulus or with an inert gas in the annulus. This radioactive detection technique can be used with individual tubing sections at the well surface. A radioactive source can also be inserted into the insulating tubing transmission conduit while in the well to determine if the tubing string contained an unacceptable number of defective joints and should be removed. Individual joints could then be tested by using this radioactive technique or by other methods to determine which joints were defective. Defective joints could then be reconditioned on-site in the manner set forth herein for reuse.

The significance of this on-site non-destructive inspection and testing and refurbishment is especially important in conjunction with means for restoring the insulating capacity of defective tubular sections and the reassembly of a fluid transmission conduit which prior to inspection, testing and refurbishment had not exhibited satisfactory insulating performance.

Although the invention has been described in terms of the specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A method of indirect, non-destructive on-site inspection, testing and repair of the insulating capacity of a tubular fluid transmission conduit installed in a subterranean well, comprising the steps of: providing a plurality of threadably interconnected concentric walled insulating tubular sections, each tubular section having an individually sealed annular insulating cavity between said concentric walls disconnecting the insulating tubular sections at the well surface; separately exposing each of said annular insulating cavity of each tubular section to a precalibrated moisture sensitive means to determine the amount of water, in the liquid and vaporous state, present in each said annular cavity; determining the insulating performance of each tubular section according to a preselected moisture level above which the tubular section is unacceptable; exposing the annular insulating cavity of each unacceptable tubular section to a vacuum means to reduce the moisture to an acceptable level; and thereafter resealing the annular insulating cavity of each such unacceptable tubular section.

* * * * *